United States Patent
Rheins et al.

(10) Patent No.: US 6,720,145 B2
(45) Date of Patent: Apr. 13, 2004

(54) METHOD FOR DETECTION OF BIOLOGICAL FACTORS IN EPIDERMIS

(75) Inventors: Lawrence A. Rheins, Escondido, CA (US); Vera B. Morhenn, La Jolla, CA (US)

(73) Assignee: Dermtech International, San Diego, CA (US)

( * ) Notice: Subject to any disclaimer, the term of this patent is extended or adjusted under 35 U.S.C. 154(b) by 112 days.

(21) Appl. No.: 09/967,658

(22) Filed: Sep. 28, 2001

(65) Prior Publication Data

US 2002/0110822 A1 Aug. 15, 2002

Related U.S. Application Data

(62) Division of application No. 09/375,609, filed on Aug. 17, 1999.
(60) Provisional application No. 60/097,025, filed on Aug. 18, 1998.

(51) Int. Cl.⁷ .......................... C12Q 1/68; C07H 21/04
(52) U.S. Cl. ...................... 435/6; 435/91.2; 536/23.5; 536/25.4; 536/25.41
(58) Field of Search .................. 435/6, 91.2; 536/23.5, 536/25.4, 25.41

(56) References Cited

U.S. PATENT DOCUMENTS

| | | | |
|---|---|---|---|
| 4,537,776 A | 8/1985 | Cooper | 514/424 |
| 4,971,800 A | 11/1990 | Chess et al. | 424/449 |
| 5,460,939 A | 10/1995 | Hansbrough et al. | 435/1.1 |
| 5,753,612 A | 5/1998 | Mitrani | 514/2 |
| 5,811,239 A | 9/1998 | Frayne | |
| 6,054,277 A | 4/2000 | Furcht et al. | |
| 6,056,859 A | 5/2000 | Ramsey et al. | |
| 6,355,439 B1 | 3/2002 | Chung et al. | 435/6 |

OTHER PUBLICATIONS

Kondo et al. Lymphokine and Cytokine Research. 1994. 13: 367–375.*
Grangsjo et al. Contact Dermatitis. 1996. 35; 355–360.*
Hoefakker et al. Contact Dermatitis. 1995. 33: 258–266.*
Brand et al. Contact Dermatitis. 1996. 35: 152–156.*
Garofano et al. Forensic Haemogenet. 1996. 6: 281–283.*
Torre et al. Journal of Forensic Sciences. 1996. 41: 658–659.*
K ndo et al. Characterization of Epidermal Cytokine Profiles in Sensitization and ellcitaion Phases of Allergic Contact dermatitis as well as Irritant Contact dermatitis in Mouse skin, Lymphokine and Cytokine R s. 1994, vol. 13, No. 6, pp. 367–375.*
Nickoloff et al. Keratinocyte Interleukin–10 Expression is Upregulated in Tape–stripped skin, poison Ivy dermatitis, and Sezary syndrome, but not in psoriatic plaques. Clinical Immunology and Immunopthology. Oct. 1994, vol. 73. No. 1, pp. 63–68.*

Farage, M.A., et al., "*Development of a Noninvasive Method for Assessing Human Skin Irritation,*" The Toxicologist (1997) vol. 36, No. 1, Part 2, pp. 365.
Nicoloff, B.J., M.D., Ph.D., et al., "*Perturbation of epidermal barrier function correlates with initiation of cytokine cascade in human skin,*" Journal of the American Academy of Dermatology (1994) vol. 30, No. 4, pp. 535–546.
Tetsuji, H., et al., "*Elevation of Interleukin I Receptor Antagonist in the Stratum Corneum of Sun–exposed and Ultraviolet B–irradiated Human Skin,*" The Journal of Investigative Dermatology (1996) vol. 106, No. 5, pp. 1102–1107.
Weigand, D.A., M.D., et al., "*Removal of Stratum Corneum In Vivo: An Improvement on the Cellophane Tape Stripping Technique,*" The Journal of Investigative Dermatology (1973) vol. 60, No. 2, pp. 84–87.
van Hoogdalem, Ewoud J., "*Assay of Erythromycin in Tape Strips of Human Stratum corneum and Some Preliminary Results in Man*" Skin Pharmacol (1992) vol. 5, pp. 124–128.
van der Molen, R.G., et al., "*Tape stripping of human stratum corneum yields cell layers that originate from various depths because of furrows in the skin,*" Archives of Dermatological Research (1997) vol. 289, pp. 514–518.
Dreber, F., et al., "*Colorimetric Method for Quantifying Human Stratum Corneum Removed by Adhesive–Tape–Stripping,*" Acta Derma Venereol (Stockholm), (1998) vol. 78, pp. 186–189.
Marttin, E., et al., "*A Critical Comparison of Methods to Quantify Stratum corneum Removed by Tape Stripping,*" Skin Pharmacology (1996) vol. 9, pp. 69–77.
Goldschmidt, H., M.D., et al., "*Desquamation of the Human Horny Layer,*" Archives of Dermatology (1967) vol. 95, pp. 583–586.
Hojyo–Tomoka, M.D., et al., "*Does Cellophane Tape Stripping Remove the Horny Layer?*" Archives of Dermatology (1972) vol. 106, No. 5, pp. 767–768.
Klaschka, F., M.D., et al., "*Individual Transparency Patterns of Adhesive–Tape Strip Series of the Stratum Corneum,*" International Journal of Dermatology (1977), vol. 16, No. 10, pp. 836–841.
Klaschka, F., et al., "*New Measuring Device of Horny Layer Transparency,*" Archives of Dermatology (1975) Vo. 254, pp. 313–325.
Katz, H.I., M.D., et al., "*Skin–Surface Touch Print for Diagnosing Fungal Infections,*" American Family Physician (1985) vol. 31, No. 4, pp. 189–194.

(List continued on next page.)

*Primary Examiner*—Carla J. Myers
(74) *Attorney, Agent, or Firm*—Gray Cary Ware & Freidenrich, LLP; Lisa A. Haile; Emanuel J. Vacchiano

(57) ABSTRACT

Disclosed is a method for removing polynucleotide from the skin. This polynucleotide can be used to detect dermatitis and distinguish an irritant reaction from an allergic reaction by characterizing the polynucleotide according to the polypeptide which it encodes. Additionally, provided are methods for non-invasive isolation of samples from the skin as well as kits for use in the methods provided herein.

4 Claims, 2 Drawing Sheets

OTHER PUBLICATIONS

Van Der Valk, P.G.M., et al., "A functional study of the skin barrier to evaporative water loss by means of repeated cellophane–tape stripping," Clinical and Experimental Dermatology (1990) vol. 15, No. 3, pp. 180–182.

Potts, R.O., et al., "Physical Methods for Studying Stratum Corneum Lipids," Seminars in Dermatology (1992) vol. 11, No. 2, pp. 129–138.

Farage, M.A., et al., "Further Development of Noninvasive Method for Assessing Human Skin Irritation," Abstract #1909, The Proctor & Gamble Company, (1998).

Cosini and Galli, "Cytokines and Irritant Contact Dermatitis," Toxicology Letters, 102–103:277–282, Elsevier (1998).

Dreher et al., "Colorimetric Method for Quantifying Human Stratum Corneum Removed by Adhesive–Tape Stripping," Acta Derma Venereol, 78:186–189, Scandinavian University Press (1998).

Farage, M.A. et al., "Further Development of Noninvasive Method for Assessing Human Skin Irritation," Abstract #1909, The Proctor & Gamble Company, (1998).

Freedberg et al., "Keratins and the Keratinocyte Activation Cycle," The Journal of Investigative Dermatology, 116(5):633–640, The Society for Investigative Dermatology, Inc. (2001).

Goldschmidt and Kligman, "Desquamation of the Human Horny Layer," Arch. Derm, 95:583–586, American Medical Association (1967).

Hamid et al., "In Vivo Expression of IL–12 and IL–13 in Atopic Dermatitis" Journal of Allergy and Clinical Immunology, 98(1):1–8, Mosby–Year Book, Inc. (1996).

Hirao et al., "Elevation of Interleukin 1 Receptor Antagonist in the Stratum Corneum of Sun–Exposed and Ultraviolet B–Irradiated Human Skin," The Journal of Investigative Dermatology, 106(5):1102–1107, The Society for Investigative Dermatology, Inc. (1996).

Hojyo–Tomoka and Kligman, "Does Cellophane Tape Stripping Remove the Horny Layer?" Arch. Derm., 106(5):767–768 (1972).

Junghans et al., "Epidermal Cytokines IL–1β, TNF–α, and IL–12 in Patients with Atopic Dermatitis: Response to Application of House Dust Mite Antigens," The Journal of Investigative Dermatology, 111(6): 1184–1188, The Society for Investigative Dermatology, Inc. (1998).

Katz et al., "Skin–Surface Touch Print for Diagnosing Fungal Infections," American Family Physician, 31(4):189–194, American Academy of Family Physicians (1985).

Klaschka and Norenberg, "Individual Transparency Patterns of Adhesive–Tape Strip Series of the Stratum Corneum," International Journal of Dermatology, 16(10):836–841, J.B. Lippincott Company (1997).

Klaschka and Nörenberg, "New Measuring Device of Horny Layer Transparency," Arch. Derm. Res., 254:313–325, Springer–Verlag (1975).

Kondo et al., "Characterization of Epidermal Cytokine Profiles in Sensitization and Elicitation Phases of Allergic Contact Dermatitis as Well as Irritant Contact Dermatitis in Mouse Skin," Lymphokine and Cytokine Research, 13(6):367–375, Mary Ann Liebert, Inc. (1994).

Marttin et al., "A Critical Comparison of Methods to Quantify Stratum corneum Removed by Tape Stripping," Skin Pharmacol., 9:69–77 S. Karger AG (1996).

Nickoloff and Naidu, "Perturbation of Epidermal Barrier Function Correlates with Initiation of Cytokine Cascade in Human Skin," Journal of the American Academy of Dermatology, 30(4):535–546, American Academy of Dermatology, Inc. (1994).

Nickoloff et al., "Keratinocyte Interleukin–10 Expression is Upregulated in Tape–Stripped Skin, Poison Ivy Dermatitis, and Sezary Syndrome, but Not in Psoriatic Plaques," Clinical Immunology and Immunopathology, 73(1):63–68, Academic Press, Inc. (1994).

Ohmen et al., "Overexpression of IL–10 in Atopic Dermatitis," The Journal of Immunology, 154:1956–1963, The American Association of Immunologists (1995).

Perkins et al., "Development of a Noninvasive Method for Assessing Human Skin Irritation," The Toxicologist, 36(1):365, Academic Press, Inc. (1997).

Perkins et al., "A Noninvasive Method to Assess Skin Irritation and Compromised Skin Conditions Using Simple Tape Adsorption of Molecular Markers of Inflammation," Skin Res. Technol., 7(4):227–237 (2001).

Potts and Francoeur, "Physical Methods for Studying Stratum Corneum Lipids," Seminars in Dermatology, 11(2):129–138, W.B. Saunders Company (1992).

Ryan and Gerberick, "Cytokine mRNA Expression in Human Epidermis after Patch Treatment with Rhus and Sodium Lauryl Sulfate," American Journal of Contact Dermatitis, 10(3):127–135, W.B. Saunders Company (1999).

van der Molen et al., Tape Stripping of Human Stratum Corneum Yields Cell Layers that Originate from Various Depths because of Furrows in the Skin, Arch. Dermatol. Res., 289:514–518, Springer–Verlag (1997).

van der Valk and Maibach, "A Functional Study of the Skin Barrier to Evaporative Water Loss by Means of Repeated Cellophane–Tape Stripping," Clinical and Experimental Dermatology, 15(3):180–182 (1990).

van Hoogdalem, "Assay of Erythromycin in Tape Strips of Human Stratum corneum and some Preliminary Results in Man," Skin Pharmacol., 5:124–128, S. Karger AG (1992).

Weigand and Gaylor, "Removal of Stratum Corneum in Vivo: An Improvement on the Cellophane Tape Stripping Technique," The Journal of Investigative Dermatology, 60(2)84–87, The Williams & Wilkins Co. (1973).

Yawalkar and Pichler, "Pathogenesis of Drug–Induced Exanthema," Int. Arch. Allergy Immunol., 124:336–338, S. Karger AG (2001).

Paludan, K. and Thestrup–Pedersen, K., "Use of the Polymerase Chain Reaction in Quantification of Interleukin 8 mRNA in Minute Epidermal Samples", The Journal of Investigative Dermatology, vol. 99, No. 6, Dec. 1992.

Torre and Gino, "Epidermal Cells on Stubs Used for Detection of GSR with SEM–EDX: Analysis of DNA Polymorphisms," Journal of Forensic Sciences, JFSCA, vol. 41, No. 4, Jul. 1996, pp. 658–659.

Garofano, L. et al., "PCR based analysis of epidermal cells found on adhesive tape," Advances in Forensic Haemogenetic, vol. 6, 1996, pp. 281–283. (Istituto di Anatomia e Fisiologia Umana, Universita degli Studi ti Torino, Italy).

Garofano, L. et al., "Comparison of Powerplex® 16 System and Other Multiplex STR Typing Kits on Casework," (Reporto Carabinieri Investigazioni Scientifiche, Parma Italia.), 2000. Reference available at: http://www.promega.com/geneticidproc/ussymp11proc/default.htm.

* cited by examiner

METHOD FOR DETECTION OF BIOLOGICAL FACTORS IN EPIDERMIS

CROSS REFERENCE TO RELATED APPLICATIONS

This application is a divisional under 35 U.S.C. §120 of U.S. application Ser. No. 09/375,609, filed Aug. 17, 1999, now pending, which claims priority under 35 U.S.C. §119(e) of Provisional Application Serial No. 60/097,025, filed Aug. 18, 1998, each of which is incorporated herein by reference in its entirety

FIELD OF THE INVENTION

This invention relates to method of detecting biological factors in epidermis, wherein the biological factor may be a polynucleotide or polypeptide encoded by the polynucleotide or a lipid.

BACKGROUND OF THE INVENTION

Cells and tissues are influenced by endogenous and exogenous agents and respond with a cascade of biological activities to mediate a response to an agent. For example, the skin is the site of many dermatological reactions that result from exposure of the skin to exogenous agents. The skin also is the most accessible organ in the body. Thus, the skin lends itself to access for determination of protein reactions, as well as, the gene(s) and gene products that are associated with or give rise to a particular reaction.

The epidermis is the outermost layer of the skin. This layer contains four major cell types. The most prevalent cell in the epidermis is the keratinocyte in various stages of differentiation. The epidermis maintains its pool of keratinocytes by mitosis of these cells in the basal cell layer, the lowest layer of the epidermis. By contrast, the upper most covering layer of the epidermis is the stratum corneum that, in normal skin, does not contain nucleated cells. Keratinocytes produce a number of cytokines including interleukin (IL) IL-I, IL-3, IL-4, IL-6, IL-7, IL-8, IL-10, IL-12 and granulocyte macrophage colony stimulating factor (GM-CSF) Kupper, M., 1993. *Am. J. Dermatopathol.* 11:69–73). Above the basal cell layer, resides the Langerhans cell, an immune competent cell of bone marrow origin. The Langerhans cell has features of macrophage as well as T cells and is thought to be responsible for initiating a series of events that lead to immune reactions in the skin such as a contact dermatitis. The melanocyte is the pigment producing cell of the skin. This cell also usually resides in the deeper layers of the epidermis. The fourth cell in the epidermis is the Merkel cell.

Immediately below the epidermis, resides the dermal layer which contains mainly fibroblasts, lymphocytes, mast cells, endothelial cells and nerve endings. Fibroblasts are the main cell type that deposit extracellular matrix material and structural proteins of the skin, such as collagen. The endothelial cells coat the lumina of the dermal capillaries and mast cells contain histamine that can be liberated in inflammatory responses of the skin. Inflammation of the skin may result from a broad array of external agents applied to the skin. Classes of contact dermatitis include irritant, allergic, photoallergic and phototoxic and subclinical mechanisms. Clinically, the reactions are virtually identical with the appearance of an eczematous process typified by erythema, edema and vesiculation (Hoefakker et al. 1995. *Contact Dermat.* 33:258–266; Krasteva, M. 1993. *Int. J. Dermatol.* 32:547–560). Contact uricaria is an additional potential response to skin application of various agents that differs in the immediate appearance of a wheal upon skin contact. Categorizing the mechanism of the contact reaction is of importance to patients. This stems from the immunologic consequences of an allergic or immune response leading to increasingly severe inflammation of the skin with re-exposure after sensitization. For example, characterizing the type of inflammatory response to exposure of an agent can provide both patients and manufacturers the ability to purchase and redesign products to avoid future inflammatory reactions.

The frequent and historical occurrence of contact dermatitis has provided the impetus for implementation of human skin testing for all new topical drugs or cosmaceuticals. A well defined arsenal to skin safety tests is now required to be conducted before any product destined to contact the skin can be put on the market in many countries. Predictive skin patch tests conducted with the product and its constituents have been the mainstay of this testing procedure. Since the inception of this predictive skin patch testing, a major deficiency has been the inability to clearly differentiate an irritant contact dermatitis (ICD) from an allergic contact dermatitis (ACD). Furthermore, the patch test is simply not sufficient for quantitatively measuring the severity of a reaction with its reliance on qualitative visual scores of erythema, edema, and vesiculation.

SUMMARY OF THE INVENTION

It is an object of the present invention to overcome the limitations described above. Thus, the present invention provides a method for non-invasively detecting a biological factor in skin cells below the stratum corneum. Characterization of the biological factor is useful in distinguishing systemic reactions as well as local reactions such as contact dermatitis and, more specifically, to distinguish irritant contact dermatitis (ICD) from allergic contact dermatitis (ACD).

In another embodiment, the invention provides a non-invasive method for obtaining a sample of polynucleotide for subsequent testing of the sample for contact dermatitis. In one preferred embodiment the stratum corneum of the epidermal layer of the skin is removed, such as by scraping with a rigid surface. In another preferred embodiment the epidermis is contacted one or more times with an adhesive surface.

In another embodiment, the invention provides a method of diagnosing ICD in a subject by quantifying a polynucleotide encoding IL-8 in sub-stratum corneum cells from the subject, wherein the presence of IL-8 mRNA in the relative absence of IL-4 of IL-13 is indicative of ICD.

In another embodiment, the invention provides a method of diagnosing ACD in a subject by quantifying polynucleotide encoding IL-4 from sub-stratum corneum cells from the subject, wherein the presence of IL-4 mRNA is indicative of ACD.

In addition, the invention, provides a method for obtaining polynucleotides from the cells below the stratum corneum of the skin of a subject, the method comprising removing the stratum corneum to expose a viable surface and collecting polynucleotide from the exposed surface.

In another embodiment, the invention provides a method of diagnosing ACD by detecting expression of IL-13 in a subject comprising quantifying polynucleotide encoding IL-13 in skin cells from the subject, wherein an elevated amount of IL-13 polynucleotide is indicative of ACD.

In another embodiment, the invention provides a kit for non-invasively obtaining samples from the skin comprising a cell collection device, such as a rigid surface or an adhesive tape, and a cell lysis buffer or computer chip suitable for preserving nucleic acids in the skin sample.

In another embodiment, the invention provides a kit comprising a cell collection device, a cell lysis buffer and a detection reagent, such as a hybridization reagent.

In a further embodiment, the invention provides a method for identifying a compound that causes a dermatitis by contacting a section of skin with a test compound and subsequently detecting the presence of a polynucleotide encoding a cytokine or a cytokine polypeptide, wherein the presence of the polynucleotide or polypeptide is indicative of a dermatitis. The method of this embodiment may be carried out in vivo or in vitro, including utilizing three-dimensional organotypic skin constructs.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
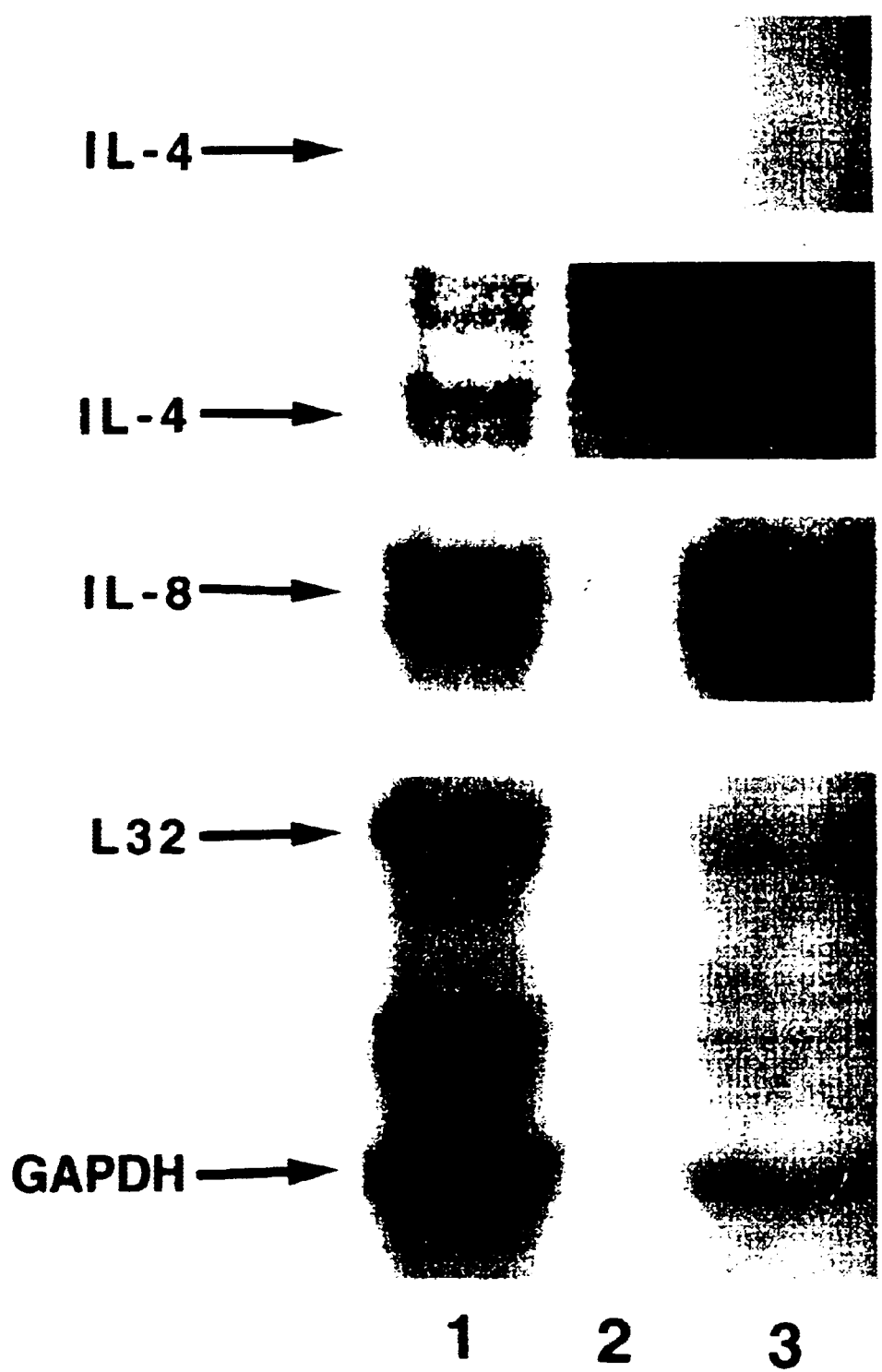
FIG. 1 depicts an exposure of a gel representing the results for ribonuclease protection assay (RPA) performed with RNA obtained by tape stripping three different areas of the upper arms of the same subject. Each of the three sites were stripped 12 times. Four different RNA probes (IL-4, IL-8, L32, GADPH) were used for hybridization to RNA samples obtained from the subject. Lane 1 shows the RNA isolated from an erythematous area of skin, read clinically as 2+ erythema that was induced by squarate (ACD). Shown in lane 3 is the RNA isolated from an ICD erythematous site (scored 2+) induced by 0.5% sodium lauryl sulfate (SLS). Both lanes demonstrate a band for IL-8. Lane 2 represents sample obtained from non-inflamed, normal appearing skin of the same subject. A band for the cytokine, IL-4, can be seen in lane 1 which was derived from an allergic reaction.

The invention provides a non-invasive method for collecting a biological factor, such as polynucleotide, from skin cells below the stratum corneum. These biological factors can then be characterized to indicate the presence of a local or systemic response in the subject. Furthermore, the invention provides a method of distinguishing all types of contact dermatitis, including subclinical. In a preferred embodiment the present invention relates to a method for distinguishing an irritant reaction from an allergic reaction by detecting a biological factor, for example a polynucleotide encoding a cytokine, obtained from the skin. In one embodiment samples containing nucleic acids are obtained non-invasively.

Inflammatory reactions often have similar clinical manifestations. In order to properly treat a patient presenting an inflammatory reaction proper identification of the reaction must be made. A "similar clinical manifestation" means that two or more reactions have a similar overall, in-gross, clinical and/or histological appearance. For example, contact dermatitis in the skin may result from a broad array of external agents which come in contact with the skin. Classes of contact dermatitis include irritant, allergic, photoallergic and phototoxic and subclinical mechanisms. Clinically, the reactions are virtually identical in appearance to an eczematous process typified by erythema, edema and vesiculation. The erythema, edema and vesicle formation of ICD and ACD may be indistinguishable. Even histologically, the two processes may only show subtle differences and these only during the first 24 hours of the reaction.

As used herein, the terms "nucleic acid," "polynucleotide," or "nucleic acid sequence" refer to a polymer of deoxyribonucleotides or ribonucleotides, in the form of a separate fragment or as a component of a larger construct. Polynucleotide or nucleic acid sequences of the invention include DNA, RNA, including mRNA and cDNA sequences.

As used herein, the term "polypeptide" refers to a polymer of amino acid residues in the form of a separate fragment or component of a larger construct. An example of a polypeptide includes amino acid sequences encoding a cytokine or fragments thereof. A polypeptide may encode for a functional protein or fragments of a protein. For example, an IL-4 polypeptide includes the full length protein sequence of IL-4 as well as fragments thereof consisting of a polymer of amino acids.

"Cytokine" as used herein means any number of factors that play a role in cellular regulation or differentiation. For example, cytokines can include the family of interleukins (IL) including IL-1, IL-2, IL-3, IL-4, IL-5, IL-6, IL-8, IL-9, IL-13, IL-14 as well as factors belonging to the transforming growth factor beta (TGF-$\beta$) superfamily, GM-CSF and interferon.

As used herein, the term "biological factor" means a number of factors that have biological activity or play a biological role. For example, biological factor includes polynucleotides, such as DNA, RNA, mRNA and cDNA, polypeptides, such as IL-4, IL-8, and IL-13 proteins and fragments thereof, as well as lipids such as cholesterol, fatty acids, and inflammatory mediators such as leukotrienes, prostaglandins and others.

The term "skin" means a tissue comprising a sheet of cells, one or several layers thick, organized above a basal lamina, and often specialized for mechanical protection or active transport. In a preferred embodiment, the skin is mammalian skin. In a more preferred embodiment the skin is human skin. The epidermis of the human skin comprises several distinct layers of skin tissue. The deepest layer is the stratum basalis layer, which consists of columnar cells. The overlying layer is the stratum spinosum, which is composed of polyhedral cells. Cells pushed up from the stratum spinosum are flattened and synthesize keratohyalin granules to form the stratum granulosum layer. As these cells move outward, they lose their nuclei, and the keratohyalin granules fuse and mingle with tonofibrils. This forms a clear layer called the stratum lucidum. The cells of the stratum lucidum are closely packed. As the cells move up from the stratum lucidum, they become compressed into many layers of opaque squamae. These cells are all flattened remnants of cells that have become completely filled with keratin and have lost all other internal structure, including nuclei. These squamae constitute the outer layer of the epidermis, the stratum corneum. At the bottom of the stratum corneum, the cells are closely compacted and adhere to each other strongly, but higher in the stratum they become loosely packed, and eventually flake away at the surface.

The term "sample" refers to any preparation derived from skin of a subject. For example, a sample of cells obtained using the non-invasive method described above may be used to isolate polynucleotides, polypeptides, or lipids. In addition, the method of the invention can be used in vitro, for example with skin cells cultured on a solid or semi-solid support and organotypic skin constructs. In such instances, the skin cells may be from any source. A biological factor obtained from any in vitro or in vivo specimen, in purified or nonpurified form, can be used as the starting material for detection of a biologic activity, such as a dermatitis, provided it contains the biological factor of interest. For example, a sample may be used to detect a dermatitis by detecting polynucleotides, provided it contains, or is suspected of containing, the specific polynucleotide sequence encoding a polypeptide, such as a cytokine, which is indicative of a dermatitis.

Samples from a tissue may be isolated by any number of means well known in the art. Invasive methods for isolating a sample include the use of needles, for example during blood sampling, as well as biopsies of various tissues. Due to the invasive nature of these techniques there is an increased risk of mortality and morbidity. The present invention provides a method and kit useful for non-invasively obtaining a sample which may be used as a source for obtaining biological factors in the detection, diagnosis, or prognosis of various diseases, disorders, or inflammatory reactions. In a preferred embodiment the invention provides a non-invasive method for obtaining a skin sample for use in isolating biological factors, for example nucleic acids and/or polypeptides, to detect a dermatitis reaction. In this embodiment epidermal cells of the skin are scraped with a rigid instrument, for example a sterile #15 scalpel, however, it will be recognized that any number of rigid instruments capable of removing only the surface layer (i.e., stratum corneum) of the skin may be used. Alternatively, instead of scraping the skin, the skin's epidermal layer may be removed by using an adhesive tape, for example, Duct tape (333 Duct tape, Nashua tape products) or Scotch® tape (3M Scotch 810, St. Paul, Minn.). However, a preferred method is to use D-SQUAME® (CuDerm, Dallas, Tex.) to strip the skin cell layer. In this embodiment the skin is stripped with the tape and the stripped cells and cellular material are then recovered from the scalpel, tape or other item. For example, tape used to obtain skin cells and cellular material may be centrifuged in a sterile microfuge tube containing lysis buffer. In the case of the scalpel the cells and cellular material may be transferred to a sterile petri dish and any cells present lysed therein with lysis buffer. The same lysis buffer may be reused for each piece of tape or scalpel used at a single skin site. For certain applications, the tape stripping method can be combined with the scraping method for removing cells and cellular material from the skin. The sample obtained may then be further processed, for example to isolate nucleic acids, polypeptides, or lipids. Preferably, the method utilized does not adversely affect the polynucleotide, polypeptide, or lipid level being measured. The invention provides, a rapid, non-invasive method for obtaining polynucleotides, such as mRNA, which are helpful to establish changes in the synthetic patterns of the skin's cells. The process of tape stripping itself has been shown not to affect the skin cytokine profile during the first few hours after the procedure is done. Using the scrapping and stripping methods of the present invention the presence of a local or systemic disease, disorder, or inflammatory reaction may be identified, distinguished, or diagnosed, including genetic diseases. In the invention any reaction, disease, or disorder that corresponds to an induction of transcription and polypeptide synthesis may be detected by the methods of the invention.

Polynucleotides can be isolated from the lysed cells and cellular material by any number of means well known to those skilled in the art. For example, a number of commercial products are available for isolating polynucleotides, including but not limited to, TriReagent (Molecular Research Center, Inc, Cincinnati, Ohio) may be used. The isolated polynucleotides can then be tested or assayed for particular nucleic acid sequences, including a polynucleotide encoding a cytokine.

In another embodiment, polypeptides may be obtained from the sample by methods known to those of skill in the art. For example, gross preparations of cells obtained using the non-invasive techniques of the invention contain polypeptides. Alternatively, the polypeptides may be further isolated or purified using conventional means including preparative chromatography and immunological separations involving monoclonal or polyclonal antibodies. The polypeptides may then be characterized to indicate the presence of a dermatatic reaction.

In one embodiment, the invention provides a method for distinguishing an irritant reaction from an allergic reaction in a skin sample by detecting a polynucleotide encoding a cytokine. The relative quantity of certain cytokines with respect to a normal or standard tissue sample distinguishes the type of reaction and/or the reactions severity.

While existing clinical tests may not be able to distinguish an irritant reaction from an allergic reaction in the tissue, the non-invasive method of the present invention is capable of distinguishing between the two reactions by their relative cytokine expression profiles. Irritant contact dermatitis can be distinguished from allergic contact dermatitis by the presence or absence of a polynucleotide encoding a cytokine or the cytokine polypeptide.

For example, in the present invention, cells from ICD had undetectable levels of polynucleotide encoding IL-4 compared with polynucleotides from cells of ACD lesions according to the method used. Consequently, the process may employ, for example, DNA or RNA, including messenger RNA (mRNA), isolated from a tissue. The DNA or RNA may be single stranded or double stranded. When RNA is obtained, enzymes and conditions optimal for reverse transcribing the template to DNA well known in the art can be used. Alternatively, the RNA can be subjected to RNAse protection assays. A DNA-RNA hybrid that contains one strand of each may also be used. A mixture of polynucleotides may also be employed, or the polynucleotides produced in a previous amplification reaction, using the same or different primers may be so used. In the instance where the polynucleotide sequence is to be amplified the polynucleotide sequence may be a fraction of a larger molecule or can be present initially as a discrete molecule, such that the specific sequence is the entire nucleic acid. It is not necessary that the sequence to be amplified be present initially in a pure form; it may be a minor fraction of a complex mixture, such as contained in whole human DNA.

In addition, RNAse protection assays may be used if RNA is the polynucleotide obtained from the sample. In this procedure, a labeled antisense RNA probe is hybridized to the complementary polynucleotide in the sample. The remaining unhybridized single-stranded probe is degraded by ribonuclease treatment. The hybridized, double stranded probe is protected from RNAse digestion. After an appropriate time, the products of the digestion reaction are collected and analyzed on a gel (see for example Ausubel et al., CURRENT PROTOCOLS IN MOLECULAR BIOLOGY, section 4.7.1 (1987)). As used herein, "RNA probe" refers to a ribonucleotide capable of hybridizing to RNA in a sample of interest. Those skilled in the art will be able to identify and modify the RNAse protection assay specific to the polynucleotide to be measured, for example, probe specificity may be altered, hybridization temperatures, quantity of nucleic acid etc. Additionally, a number of commercial kits are available, for example, RiboQuantTM Multi-Probe RNAse Protection Assay System (Pharmingen, Inc., San Diego, Calif.).

In another embodiment, the polynucleotide in the sample may be analyzed by Northern or Southern blot. In this technique the polynucleotides are separated on a gel and then probed with a complementary polynucleotide to the sequence of interest. For example, RNA is separated on a gel transferred to nitrocellulose and probed with complementary DNA to the sequence of interest. The complementary probe may be labeled radioactively, chemically etc. Hybridization of the probe is indicative of the presence of the polynucleotide of interest.

Detection of a polynucleotide encoding a cytokine may be performed by standard methods such as size fractionating the nucleic acid. Methods of size fractionating the DNA and RNA are well known to those of skill in the art, such as by gel electrophoresis, including polyacrylamide gel electrophoresis (PAGE). For example, the gel may be a denaturing 7 M or 8 M urea-polyacrylamide-formamide gel, Size fractionating the nucleic acid may also be accomplished by chromatographic methods known to those of skill in the art.

The detection of polynucleotides may optionally be performed by using radioactively labeled probes. Any radioactive label may be employed which provides an adequate signal. Other labels include ligands, colored dyes, and fluorescent molecules, which can serve as a specific binding pair member for a labeled ligand, and the like. The labeled preparations are used to probe for a polynucleotide by the Southern or Northern hybridization techniques, for example. Nucleotides obtained from samples are transferred to filters that bind polynucleotides. After exposure to the labeled polynucleotide probe, which will hybridize to nucleotide fragments containing target nucleic acid sequences, the binding of the radioactive probe to target nucleic acid fragments is identified by autoradiography (see *Genetic Engineering*, 1 ed. Robert Williamson, Academic Press (1981), pp. 72–81). The particular hybridization technique is not essential to the invention. Hybridization techniques are well known or easily ascertained by one of ordinary skill in the art. As improvements are made in hybridization techniques, they can readily be applied in the method of the invention.

The polynucleotides encoding the desired polypeptide may be amplified before detecting. The term "amplified" refers to the process of making multiple copies of the nucleic acid from a single polynucleotide molecule. The amplification of polynucleotides can be carried out in vitro by biochemical processes known to those of skill in the art. The amplification agent may be any compound or system that will function to accomplish the synthesis of primer extension products, including enzymes. Suitable enzymes for this purpose include, for example, E. coli DNA polymerase I, Taq polymerase, Klenow fragment of E. coli DNA polymerase I, T4 DNA polymerase, other available DNA polymerases, polymerase muteins, reverse transcriptase, ligase, and other enzymes, including heat-stable enzymes (i.e., those enzymes that perform primer extension after being subjected to temperatures sufficiently elevated to cause denaturation). Suitable enzymes will facilitate combination of the nucleotides in the proper manner to form the primer extension products that are complementary to each mutant nucleotide strand. Generally, the synthesis will be initiated at the 3'-end of each primer and proceed in the 5'-direction along the template strand, until synthesis terminates, producing molecules of different lengths. There may be amplification agents, however, that initiate synthesis at the 5'-end and proceed in the other direction, using the same process as described above. In any event, the method of the invention is not to be limited to the embodiments of amplification described herein.

One method of in vitro amplification which can be used according to this invention is the polymerase chain reaction (PCR) described in U.S. Pat. Nos. 4,683,202 and 4,683,195. The term "polymerase chain reaction" refers to a method for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. The polymerase chain reaction is used to detect the presence of polynucleotides encoding cytokines in the sample. Many polymerase chain methods are known to those of skill in the art and may be used in the method of the invention. For example, DNA can be subjected to 30 to 35 cycles of amplification in a thermocycler as follows: 95° C. for 30 sec, 52° to 60° C. for 1 min, and 72° C. for 1 min, with a final extension step of 72° C. for 5 min. For another example, DNA can be subjected to 35 polymerase chain reaction cycles in a thermocycler at a denaturing temperature of 95° C. for 30 sec, followed by varying annealing temperatures ranging from 54–58° C. for 1 min, an extension step at 70° C. for 1 min and a final extension step at 70° C.

The primers for use in amplifying the polynucleotides of the invention may be prepared using any suitable method, such as conventional phosphotriester and phosphodiester methods or automated embodiments thereof so long as the primers are capable of hybridizing to the polynucleotides of interest. One method for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers used according to the method of the invention are complementary to each strand of nucleotide sequence to be amplified. The term "complementary" means that the primers must hybridize with their respective strands under conditions which allow the agent for polymerization to function. In other words, the primers that are complementary to the flanking sequences hybridize with the flanking sequences and permit amplification of the nucleotide sequence. Preferably, the 3' terminus of the primer that is extended has perfectly base paired complementarity with the complementary flanking strand.

Those of ordinary skill in the art will know of various amplification methodologies which can also be utilized to increase the copy number of target nucleic acid. The polynucleotides detected in the method of the invention can be further evaluated, detected, cloned, sequenced, and the like, either in solution or after binding to a solid support, by any method usually applied to the detection of a specific nucleic acid sequence such as another polymerase chain reaction, oligomer restriction (Saiki et al., *Bio/Technology* 3:1008–1012 (1985)), allele-specific oligonucleotide (ASO) probe analysis (Conner et al., *Proc. Natl. Acad. Sci. USA* 80: 278 (1983), oligonucleotide ligation assays (OLAs) (Landegren et al., *Science* 241:1077 (1988)), RNAse Protection Assay and the like. Molecular techniques for DNA analysis have been reviewed (Landegren et al, *Science* 242: 229–237 (1988)). Following DNA amplification, the reaction product may be detected by Southern blot analysis, without using radioactive probes. In such a process, for example, a small sample of DNA containing the polynucleotides obtained from the tissue or subject are amplified, and analyzed via a Southern blotting technique. The use of non-radioactive probes or labels is facilitated by the high level of the amplified signal. In one embodiment of the invention, one nucleoside triphosphate is radioactively labeled, thereby allowing direct visualization of the amplification product by autoradiography. In another embodiment, amplification primers are fluorescently labeled and run through an electrophoresis system. Visualization of amplified products is by laser detection followed by computer assisted graphic display, without a radioactive signal.

Simple visualization of a gel containing the separated products may be utilized to determine the presence or severity of a dermatitis reaction. For example, staining of a gel to visualize separated polynucleotides, a number of stains are well known to those skilled in the art. However, other methods known to those skilled in the art may also be used, for example scanning densitometry, computer aided scanning and quantitation as well as others.

Thus, the methods described above can be used to non-invasively obtain a sample of tissue from a subject suspected of having dermatitis, such as an irritant or allergic reaction, and isolate polynucleotides from the sample. The polynucleotides can then be analyzed using methods such as, but not limited to, those described above. Any number of cytokine levels can be quantified by measuring their relative expression in the sample obtained and comparing these levels to normal-standard samples. For example, the mRNA level(s) in a cell change when the production of proteins in the skin are either increased or reduced. Thus, a measurement of RNA, in particular mRNA, provides a monitor of event(s) such as inflammatory reactions occurring in the skin or as a result of a local or systemic response. It will be recognized that the present non-invasive techniques are capable of detecting any reaction, disorder, or disease so long as the biological factor is present in the skin, more particularly below the stratum corneum of the skin. For example, and not by way of limitation, the inventors have discovered that polynucleotide encoding the cytokine IL-4 can be detected at higher levels in allergic contact dermatitis (ACD) lesions than in normal skin or skin from an ICD lesion. In addition, the inventors have discovered that polynucleotide encoding IL-13 is at a higher concentration in ACD skin than in normal or ICD skin. In contrast polynucleotide encoding IL-8 is at higher levels in both ACD and ICD compared to normal skin. Thus, elevated levels of IL-8 polynucleotide can be used diagnostically to detect a general contact dermatitis. By using the methods of the invention it is possible to quantify the severity of a reaction by measuring the levels of polynucleotides encoding cytokines when compared to a normal-standard sample.

The method for detecting a cytokine for distinguishing dermatitis reactions may alternatively employ the detection of a cytokine polypeptide. The method for detecting a cytokine polypeptide in cells is useful for distinguishing a reaction by measuring the level of a particular cytokine, for example IL-4, IL-8 and/or IL-13, in cells obtained from a subject suspected of having a dermatitis reaction. The levels of such cytokines are indicative of a reaction when compared to a normal or standard cytokine polypeptide profile in a similar tissue. Thus, the expression pattern of a cytokine polypeptide will vary depending upon the type and degree of a dermatitis reaction. In this regard, the sample obtained, as described herein, may be used as a source to isolate polypeptides. Measurement of a particular polypeptide, for example IL-4, may serve as a method of identifying ACD. For example, following skin scraping or skin stripping, using the methods described above, cells isolated from the stratum corneum may be lysed by any number of means, and polypeptides obtained from the cells. These polypeptides may then be quantified using methods known to those of skill in the art, for example by ELISA.

Monoclonal antibodies to a particular polypeptide, for example, IL-4, IL-8, IL-13 and others, can be used in immunoassays, such as in liquid phase or bound to a solid phase carrier, to detect polypeptide associated with a disorder, such as dermatitis. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the polypeptide antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation. In addition, there are a number of commercially available antibodies to cytokines of interest.

The term "immunometric assay" or "sandwich immunoassay" includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

Monoclonal antibodies can be bound to many different carriers and used to detect the presence of a cytokine polypeptide. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

A cytokine polypeptide may be detected by the monoclonal antibodies when present in biological fluids and tissues. Any sample containing a detectable amount of cytokine can be used. A sample can be a liquid such as blood, serum and the like, or a solid or semi-solid such as tissues, skin sample, or, alternatively, a solid tissue such as those commonly used in histological diagnosis.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-cytokine immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays.

It has been found that a number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1–100 $\mu g/\mu l$) may be important, in order to maintain the proper sensitivity yet inhibit any unwanted interference by mutually occurring cross reactive proteins in the specimen.

In another embodiment the invention provides a kit for non-invasively obtaining samples from the skin comprising a cell collection device selected from the group consisting of a rigid surface, an adhesive tape, or both and a cell lysis buffer suitable for preserving nucleic acids in the skin sample. In another embodiment the invention provides a kit comprising a cell collection device, a cell lysis buffer and an mRNA detection reagent for distinguishing irritant and allergic reactions in a tissue. The kit comprises a polynucleotide detection reagent, for example an oligonucleotide primer that is complementary to a polynucleotide sequence encoding a cytokine, such as IL-4. Such a kit may also include a carrier means being compartmentalized to receive in close confinement one or more containers such as vials, tubes, and the like, each of the containers comprising one of the separate elements to be used in the method. If present, a second container may comprise a lysis buffer. The kit may alternatively include a computer-type chip on which the lysis of the cell will be achieved by means of an electric current.

The kit may also have containers containing nucleotides for amplification of or hybridization to the target nucleic acid sequence which may or may not be labeled, or a container comprising a reporter, such as a biotin-binding protein, such as avidin or streptavidin, bound to a reporter molecule, such as an enzymatic, florescent, or radionuclide label. The term "detectably labeled deoxyribonucleotide" refers to a means for identifying deoxyribonucleotide. For example, the detectable label may be a radiolabeled nucleotide or a small molecule covalently bound to the nucleotide where the small molecule is recognized by a well-characterized large molecule. Examples of these small molecules are biotin, which is bound by avidin, and thyroxin, which is bound by anti-thyroxin antibody. Other methods of labeling are known to those of ordinary skill in the art, including enzymatic, fluorescent compounds, chemiluminescent compounds, phosphorescent compounds, and bioluminescent compounds.

In another embodiment the invention provides a way of screening for compounds or identifying compounds which may cause a dermatitis. In this method, cells of the skin, such as epidermal cells, including keratinocytes and melanocytes, or dermal cells, such as fibroblasts, are contacted with a test compound under conditions which would induce a dermatitis reaction. The conditions under which contact is made are variable and will depend upon the type of compound, the type and amount of cells in the skin to be tested, the concentration of the compound in the sample to be tested, as well as the time of exposure to the compound. The skill in the art in determining the proper conditions under which a compound may cause a dermatitis are known and would require only routine experimentation, if any. The skin cells may be isolated using the techniques described above, e.g. by scraping or tape stripping, the cells may then be exposed to the test compound in vitro. Alternatively, cultured skin cells or skin constructs may be used. For example, skin cells may be cultured from any source under standard cell culture conditions on a solid or semi-solid support until they become sufficiently confluent. Upon confluence or subconfluence the cells are then exposed to the test compound. Polynucleotides are then isolated from the cells which have been exposed to the compound and quantitated as described above. For example, and not by way of limitation, the cells may be isolated by the tape or scraping method above and mRNA isolated. The mRNA is then quantified using the probes for particular cytokines. Alternatively, the mRNA may be RT-PCR prior to detection of the polynucleotide. As described above, quantitation of a polynucleotide encoding a cytokine is indicative of dermatitis, for example an increase in IL-4 compared to a standard sample is indicative of ACD and an increase in IL-8 without an increase in IL-4 or IL-13 is indicative of ICD.

The present invention is not to be limited in scope by the specific examples provided for below, which are intended as single illustrations of individual aspects of the invention and functionally equivalent methods and components are within the scope of the invention.

EXAMPLE 1

Non-invasive Recovery of Sub-Stratum Corneum Cells

A. Recovery Using a Rigid Surface

Skin cells can be recovered non-invasively by scraping the skin with a sterile #15 scalpel. The scalpel is held at an angle approximately 15 degrees from horizontal and repeatedly but gently scraped across an area of skin that is approximately 1×1 cm in size. The epidermal cells are transferred to a sterile tissue culture well by scraping the blade against the interior wall of the well. When the glistening epidermal layer is reached, the scraping is stopped prior to causing any bleeding, to avoid contaminating the scraping(s) with blood. The cells are deposited in a sterile 1 cm petri dish and about 300 ml of lysis buffer is added to the culture well. The lysis buffer is pipetted up and down until the epidermal cells are completely lysed.

RNA lysis buffer is added within 10 minutes of initiation of the scraping. The sterile tissue culture well is maintained on dry ice. The cells are dissolved in the RNA lysis buffer, transferred into RNAse free centrifuge tubes and the total RNA is extracted.

B. Recovery Using an Adhesive Surface

Skin cells can be recovered non-invasively by using Duct tape (333 Duct tape, Nashua tape products), Scotch® tape (3M Scotch® 8 10, St. Paul, Minn.), or D-SQUAME® (CuDerm, Dallas, Tex.). The skin is stripped up to a maximum 25 times. Additionally, it will be recognized that the stickier the tape, the fewer strippings are required. The skin cells were recovered by vortexing and then centrifuging the tape in an RNAse-free Eppendorf tube containing lysis buffer. The same lysis buffer was reused for each piece of tape used at a single skin site. The entire procedure was performed in less than 90 minutes. The process of tape stripping itself does not affect the skin cytokine profile during the first few hours after the procedure is done. Moreover, during the early hours after stripping no inflammatory cells migrate from the circulation into the dermis or epidermis.

RNA was immediately extracted from cells adhering to the strip by vigorously vortexing the tape in 0.5 ml TriReagent (Molecular Research Center, Inc., Cincinnati, Ohio). Yeast transfer RNA (4 μg) was then added as carrier RNA before the total RNA was isolated and purified according to the manufacturer's instructions. The total isolated RNA from each sample was used in an RNAse protection assay (RiboQuant® Multiprobe RNAse Protection Assay System, PharMingen, Inc., San Diego, Calif.) without prior measurement of the amount of RNA by OD measurement. Assays were performed with samples on standard acrylamide sequencing gels and used to identify digested cytokine messages. Gels containing digested RNA bands were first exposed to a Phosphor Screen (Molecular Dynamics, Inc., Sunnyvale, Calif.). The exposed screen was then scanned with a phosphorimager Storm 860 (Molecular Dynamics, Inc.). Intensities of bands in each sample were analyzed with the software ImageQuantTM (Molecular Dynamics, Inc.).

Appropriate care should be taken to prevent RNAse contamination of the samples since skin is a rich source of RNAse that can quickly degrade RNA released from damaged epidermal cells. The sample collection and extraction techniques described herein demonstrate that skin RNA can indeed be obtained without significant degradation as indicated by the ability to detect mRNA by RPA.

EXAMPLE 2

Analysis Of Cells Obtained By Tape Stripping

Irritant contact dermatitis (ICD) was induced by applying 0.5% sodium lauryl sulfate (SLS) in distilled water for 72 hours to the upper arm. After this exposure, the erythema was graded according to standard scoring sales (Fisher's Contact Dermatitis. 4th ed. Rietschel, R. L. and Fowler, J. F. Jr. eds. Williams & Wilkins, Baltimore, 1995, pg. 29). Allergic contact dermatitis (ACD) was induced by applying dibutyl squarate in acetone to the upper arm of the same subject under occlusion for 48 hours. The upper arms of the same individual (subject #1) were tape stripped 12 times and processed as described in Example 2 above.

FIG. 1, lane 1 shows the RNA isolated from an ACD erythematous area of skin, read clinically as 3+ erythema, that was induced by squarate. Lane 3 is the RNA from ICD erythematous skin, clinically scored as 2+ erythema, induced after exposure to 0.5% SLS. After exposure of the x-ray film, the band for cytokine IL-4 can be clearly seen in lane 1, but not in lane 3 which contains RNA from ICD cells. Thus, the cytokine pattern in the ACD reaction clearly differed from the ICD reaction and normal skin seen in lane 2.

Figure 2:
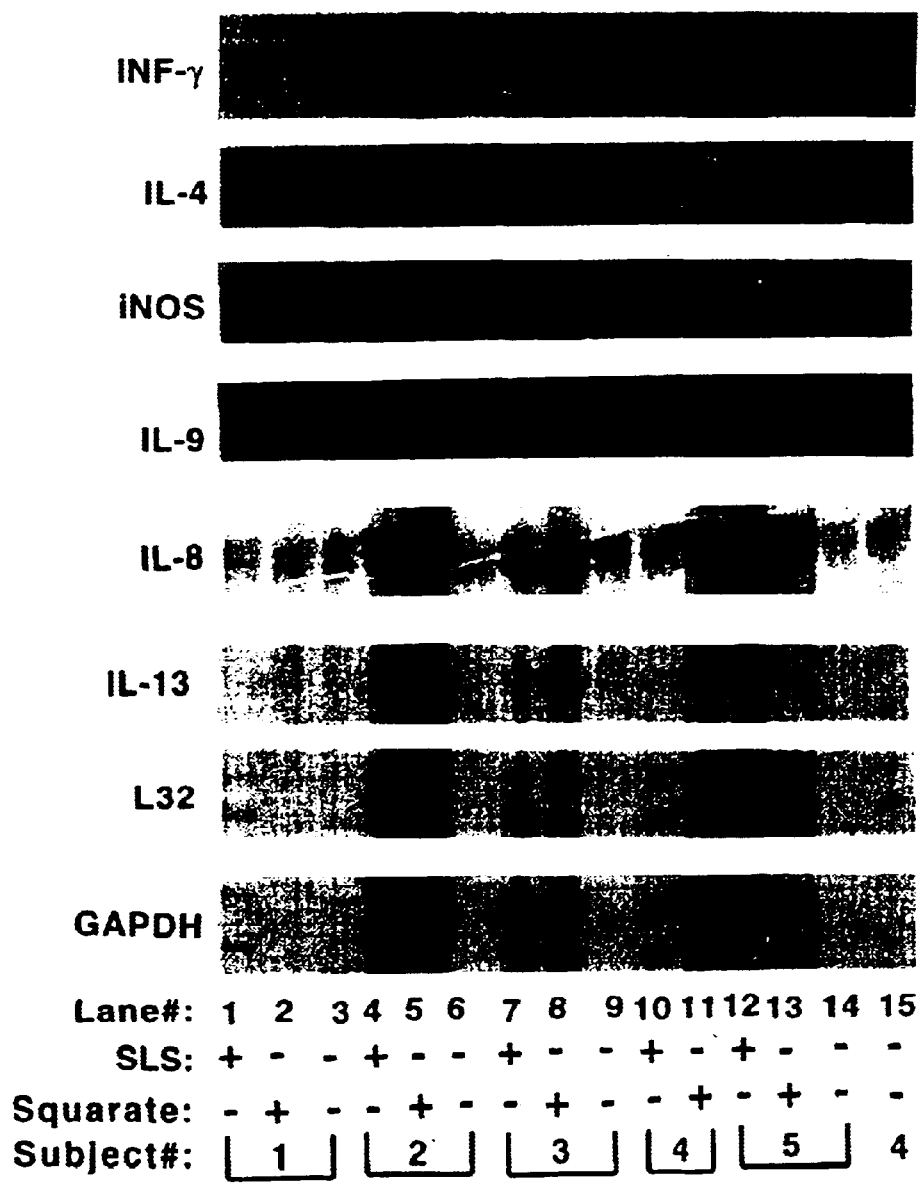
FIG. 2 are results for RPA performed with RNA obtained by tape stripping three different areas of the upper arm of four more individuals. Riboprobes for 6 different RNAs (IL-4, IL-8, IL-9, IL-13, IL-14 and an isoform of nitric oxide synthase (iNOS)) plus 2 housekeeping genes were included in this gel. The "+" indicates that the skin harvested from the subject had been treated either with SLS (second row at bottom of figure) or squarate (third row at bottom of figure).

In a subsequent experiment, all subjects with dermatitis had mRNA encoding the cytokine IL-4 in cells from skin in areas that had demonstrated an ACD reaction (lanes 8, 11, 13 in FIG. 2). By contrast, IL-4 was not visible in any of the ICD treated areas of skin or in normal skin samples obtained from the same subjects. Furthermore, in 4 of 5 subjects (subjects 2, 3, 4 and 5 in FIG. 2), IL-8 was present in erythematous areas of skin, whether the erythema was induced by an irritant or an allergic reaction, but not in the RNA obtained from normal skin. Thus, IL-8 mRNA was generically indicative of dermatitis.

The mRNA encoding IL-13, a cytokine secreted by activated T cells, was present in 3 of the 4 erythematous areas of skin (lanes 5, 8, 11, 13 in FIG. 2) in which allergic inflammation had been induced by squarate. A faint band could be seen in the approximate area(s) expected to contain the mRNA with the molecular weight associated with gamma interferon (IFN-γ) (lanes 8 and 11 in FIG. 2). These bands were present in the mRNA extracted from 2 of the 5 squarate (ACD) treated skin samples. As was the case for IL-13, the tentative band for IFN-γ mRNA was seen in the same lanes that also had mRNA for IL-4.

IL-14, a B cell growth factor, was present in some of the squarate treated skin samples as well as some of the SLS treated skin samples (FIG. 2). IL-9, a multifunctional cytokine, was detected in all 13 samples that could be visualized in this experiment. In addition, the mRNA for the inducible isoform of nitric oxide synthase (iNOS) and IL-9 were seen in every lane that could be visualized clearly (13 of 15 samples) (FIG. 2). The presence of IL-4 in the same lanes as IL-13 strongly suggests that these two cytokine markers were induced by an allergic reaction in the skin from which the samples were obtained.

The clinical quantification of the erythema visualized in the various skin reactions is documented in Tables 1 and 2.

TABLE 1

ACD REACTIONS

| SUBJEC | SKIN REACTIO | IL-4 | IL-8 | IL-9 | IL-13 | iNOS | IFNγ |
|---|---|---|---|---|---|---|---|
| #1 | 0 | ND | ND | + | ND | + | ND |
| #2 | 2+ | + | + | NT | NT | NT | NT |
| #3 | 2+ | + | + | + | + | + | + |
| #4 | 2+ | + | + | * | + | * | + |
| #5 | 2+ | + | + | + | + | + | + |

ND = not detected
2+ = moderate erythema (red)
* gel not readable
NT = not tested

TABLE 2

ICD REACTIONS

| SUBJEC | SKIN REACTIO | IL-4 | IL-8 | IL-9 | IL-13 | iNOS | IFNγ |
|---|---|---|---|---|---|---|---|
| #1 | 0 | ND | ND | + | ND | + | ND |
| #2 | 2+ | + | + | NT | NT | NT | NT |
| #3 | 1+ | ND | + | + | + | + | ND |
| #4 | 1+ (low) | ND | ND | + | ND | ND | ND |
| #5 | 3+ | * | + | * | * | * | * |

ND = not detected
1+ = mild erythema (pinkish)
* gel not readable
2+ = moderate erythema (red)
NT = not tested
3+ = strong erythema (beet red)

EXAMPLE 3

To further examine the relationship between the cytokines and the degree of inflammation in subject numbers 3–5, the IL-4, IL-8 and IL-13 RNA levels were normalized to the corresponding housekeeping gene levels (Table 3). Among the three subjects analyzed, a correlation exists between the RNA levels and the severity of the reactions. Table 2 shows that the samples from the strongest skin reactions were also the ones that demonstrated the largest relative amount of IL-8 in the ACD reaction. For example, subject #4 with a 2+ reaction at the ACD site and only a slight (low +1) reaction at the ICD site showed an approximate two fold difference in the IL-8/GAPDH ratios when comparing the ICD and ACD reactions using the RPA method described above. In addition, one would predict an ACD reaction if, on the gel, there is a band for IL-4 and a value for IL-4/GAPDH of about 0.001 or higher. Also, an ACD reaction can be confirmed where there is an IL-13 band with an IL-13/GAPDH value of about 0.13 or higher (Table 3).

TABLE 3

| Subject | | TYPE OF REACTION | |
|---|---|---|---|
| | | ICD | ACD |
| 3 | IL-4/GAPDH | NC | NC |
| | IL-8/GAPDH | 0.3495 | 0.8867 |
| | iNOS/GAPDH | 0.2202 | 0.2652 |
| | IL-13/GAPDH | 0.070 | 0.251 |
| 4 | IL-4/GAPDH | 0 | 0.01559 |
| | IL-8/GAPDH | 0.2879 | 0.61080 |
| | iNOS/GAPDH | 0.07107 | 0.2661 |
| | IL-13/GAPDH | 0.117 | 0.134 |
| 5 | IL-4/GAPDH | 0 | 0.07255 |
| | IL-8/GAPDH | 0.2541 | 1.3023 |
| | iNOS/GAPDH | 0.05315 | 0.1951 |
| | IL-13/GAPDH | 0.055 | 0.158 |

NC = not calculated

A number of embodiments of the present invention have been described. Nevertheless, it will be understood that various modifications may be made without departing from the spirit and scope of the invention. Accordingly, other embodiments are within the scope of the following claims.

What is claimed is:

1. A method of distinguishing an irritant contact dermatitis (ICD) from an allergic contact dermatitis (ACD) in human subject, comprising determining the quantity of IL-4 and IL-8 mRNA in skin cells from below the stratum corneum at 48 and 72 hours following contact with an agent, wherein an increase in the level of IL-4 relative to a control sample is indicative of ACD and wherein an increase in the level of IL-8 mRNA relative to a control sample is indicative of ICD.

2. The method of claim 1, wherein the stratum corneum is removed before determining the quantity of IL-4 and IL-8, using procedures selected from the group consisting of:

a) abrading the stratum corneum; and b) contacting the stratum corneum with an adhesive surface.

3. The method of claim 1, wherein the quantity of IL-4 and IL-8 mRNA is determined in a polynucleotide sample collected from a surface exposed after removal of the stratum corneum using a procedure selected from the group consisting of:

a) scraping the surface exposed with a rigid surface; and b) contacting the surface exposed with an adhesive surface.

4. The method of claim 3, wherein the adhesive surface comprises adhesive tape.

* * * * *